United States Patent [19]

Morita et al.

[11] 4,179,437

[45] * Dec. 18, 1979

[54] AMINO ACID DERIVATIVES OF 6-(2-AMINO-2-ARYLACETAMIDO) PENICILLANIC ACIDS

[75] Inventors: Yoshiharu Morita; Kenzo Omata, both of Yokohama; Junichi Ohya, Zama; Kazuo Wagatsuma, Yokohama; Tadashi Shirasaka, Kawasaki, all of Japan

[73] Assignee: Mitsubishi Chemical Industries Limited, Tokyo, Japan

[ * ] Notice: The portion of the term of this patent subsequent to Oct. 10, 1995, has been disclaimed.

[21] Appl. No.: 899,458

[22] Filed: Apr. 24, 1978

Related U.S. Application Data

[63] Continuation of Ser. No. 713,808, Aug. 12, 1976, Pat. No. 4,111,932.

[30] Foreign Application Priority Data

Sep. 8, 1975 [JP] Japan .................................. 50/108708

Sep. 8, 1975 [JP] Japan .................................. 50/108709
Feb. 5, 1976 [JP] Japan .................................. 51/12119
Feb. 6, 1976 [JP] Japan .................................. 51/12121
Feb. 14, 1976 [JP] Japan .................................. 51/15335
Feb. 16, 1976 [JP] Japan .................................. 51/15563

[51] Int. Cl.$^2$ ............................................. C07D 499/68
[52] U.S. Cl. ................................................ 260/239.1
[58] Field of Search ..................................... 260/239.1

[56] References Cited

U.S. PATENT DOCUMENTS

| 3,268,513 | 8/1966 | Grant et al. ........................ 260/239.1 |
| 3,340,252 | 9/1967 | Alburn et al. ..................... 260/239.1 |

*Primary Examiner*—Gerald A. Schwartz
*Attorney, Agent, or Firm*—Oblon, Fisher, Spivak, McClelland & Maier

[57] ABSTRACT

Amino acid derivatives of 6-(2-amino-2-arylacetamido) penicillanic acids are prepared and shown to be useful as antibacterial agents.

1 Claim, No Drawings

AMINO ACID DERIVATIVES OF 6-(2-AMINO-2-ARYLACETAMIDO) PENICILLANIC ACIDS

The present application is a 37 C.F.R. 1.60 continuation of Ser. No. 713,808, filed Aug. 12, 1976, in respect to the subject matter claimed herein. Ser. No. 713,808 has issued as U.S. Pat. No. 4,111,932.

BACKGROUND OF THE INVENTION

1. Field of the Invention

This invention relates to amino acid derivatives of 6-(2-amino-2-arylacetamido)penicillanic acids which are effective against Gram-negative and Gram-positive bacteria.

2. Description of the Prior Art

While many penicillins have been remarkably effective in the treatment of a variety of infections, few penicillins have been found to posess significant activity against *Psudomonas aeruginosa* and penicillin resistant *staphylococci*. There is a continuing need for different and improved penicillins.

U.S. Pat. No. 3,340,252 to Harvey E. Alburn et al., issued Sept. 5, 1967, discloses 6-[D-2-(azetidine-2-carboxamido)-2-phenylacetamido]penicillanic acid and 6-[D-2-(octamethyleneimine-2-carboxamido)-2-phenylacetamido]penicillanic acid.

SUMMARY OF THE INVENTION

Accordingly, it is an object of this invention to provide novel amino acid derivatives of 6-(2-amino-2-arylacetamido)penicillanic acids having superior antibacterial activity. This and other objects of the present invention as will hereinafter become clear have been attained by providing compounds of the formula (I):

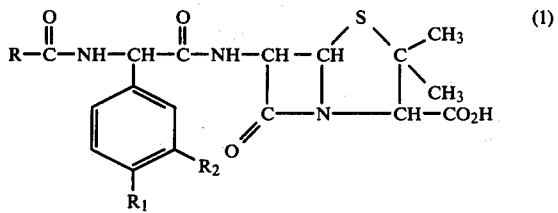

wherein $R_1$ and $R_2$ are selected from the group consisting of hydrogen, hydroxy and amino; and R is selected from the group consisting of (1)

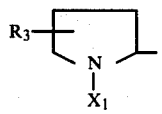

wherein $R_3$ is selected from the group consisting of hydrogen, hydroxy and oxo; and $X_1$ is hydrogen or an N-blocking group, (2)

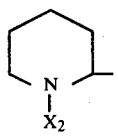

wherein $X_2$ is hydrogen or an N-blocking group, (3)

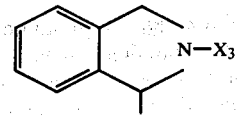

wherein $X_3$ is hydrogen or an N-blocking group, (4)

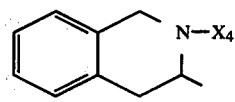

wherein $X_4$ is hydrogen or an N-blocking group, or (5)

$$X_5-\underset{\underset{CH_3}{|}}{N}-\underset{\underset{R_4}{|}}{CH}-$$

wherein $X_5$ is hydrogen or an N-blocking group; and $R_4$ is selected from the group consisting of hydrogen, methyl, isobutyl and phenyl.

Also encompassed within this invention are non-toxic, pharmaceutically acceptable salts thereof.

DETAILED DESCRIPTION OF THE PREFERRED EMBODIMENTS

As summarized above, this invention relates to a group of compounds useful as antibacterial agents, which compounds are represented by Formula I above.

Suitable illustrations of $R_1$ in the above formula (I) are hydrogen, hydroxy and amino. Especially preferred are hydrogen and hydroxy.

Suitable illustrations of $R_2$ in the above formula (I) are hydrogen and amino. Highly preferred is hydrogen.

Suitable $R_3$ groups in the above formula (I) are hydrogen, 4-hydroxy, 4-oxo and 5-oxo. Especially preferred are hydrogen, 4-hydroxy and 5-oxo.

Suitable N-blocking groups represented by $X_1$, $X_2$, $X_3$, $X_4$ or $X_5$ are benzyloxycarbonyl, p-methoxybenzyloxycarbonyl, p-nitrobenzyloxycarbonyl, t-butoxycarbonyl, t-amyloxycarbonyl, adamantyloxycarbonyl, tosyl, benzenesulfonyl and carbamoyl. Especially preferred are benzyloxycarbonyl, tosyl and carbamoyl.

Illustrative of suitable amino acid derivatives of 6-(2-amino-2-arylacetamido)penicillanic acids of sufficient activity of this invention are the following:

6-(D-2-prolylamino-2-phenylacetamido)penicillanic acid
6-[D-2-prolylamino-2-(4-hydroxyphenyl)acetamido]penicillanic acid
6-[D-2-(N-tosylprolyl)amino-2-phenylacetamido]penicillanic acid
6-[D-2-(piperidine-2-carboxamido)-2-(4-hydroxyphenyl)acetamido]penicillanic acid
6-[D-2-(1,2,3,4-tetrahydroisoquinoline-3-carboxamido)-2-phenylacetamido]penicillanic acid
6-[D-2-(isoindoline-1-carboxamido)-2-phenylacetamido]penicillanic acid
6-[D-2-(N-tosyl-N-methylalanyl)amino-2-phenylacetamido]penicillanic acid
6-[D-2-(N-tosyl-N-methylalanyl)amino-2-(4-hydroxyphenyl)-acetamido]penicillanic acid
6-[D-2-(N-methylalanyl)amino-2-(4-hydroxyphenyl)acetamido]penicillanic acid 6-[D-2-(N-tosylsarcosyl)amino-2-phenylacetamido]-
penicillanic acid
6-[D-2-(N-tosyl-N-methylleucyl)amino-2-
phenylacetamido]penicillanic acid
6-[D-2-(N-benzyloxycarbonyl-N-methylleucyl)amino-
2-phenylacetamido]penicillanic acid
6-[D-2-{2-(N-methyl-N-benzyloxycarbonyl)amino-2-
phenylacetamido}-2-phenylacetamido]penicillanic
acid
6-[D-2-{2-(N-methyl-N-tosyl)amino-2-
phenylacetamido}-2-phenylacetamido]penicillanic
acid
6-[D-2-(N-methylleucyl)amino-2-phenylacetamido]-
penicillanic acid Of the compounds of this invention, it will be understood that the following compounds are most preferred due to their high level of antibacterial activity.
6-(D-2-prolylamino-2-phenylacetamido)penicillanic
acid
6-[D-2-prolylamino-2-(4-hydroxyphenyl)acetamido]-
penicillanic acid
6-[D-2-(piperidine-2-carboxamido)-2-(4-hydroxy-
phenyl)acetamido]penicillanic acid
6-[D-2-(1,2,3,4-tetrahydroisoquinoline-3-carboxamido)-
2-phenylacetamido]penicillanic acid
6-[D-2-(N-tosyl-N-methylalanyl)amino-2-
phenylacetamido]penicillanic acid
6-[D-2-(N-methylalanyl)amino-2-(4-hydroxyphenyl-
)acetamido]penicillanic acid
6-[D-2-(N-benzyloxycarbonyl-N-methylleucyl)amino-
2-phenylacetamido]penicillanic acid Also included within the scope of this invention are the non-toxic cationic, e.g., the pharmaceutically acceptable salts of the compounds of this invention. Such salts include, for example, sodium, potassium, calcium, magnesium, ammonium and substituted ammonium salts, e.g., procaine, N,N'-dibenzylethylenediamine.

As one skilled in the art can readily appreciate, the compounds of this invention are sufficiently basic, by virtue of the imino or amino group in the amino acid moiety, to form acid addition salts; said salts, especially the pharmaceutically acceptable acid addition salts, are also considered within the scope of this invention. Such salts include, for example, inorganic salts such as hydrochlorides and sulfates, and organic salts such as fumarates, malates and formates.

The penicillin derivatives of this invention are capable of existing in two optically active isomers, the D- and L-diastereoisomers, as well as the racemate, DL-mixture, since there is usually a center of asymmetry in the radical R. The various forms as well as their mixtures are within the scope of this invention. Ordinarily, the penicillin derivatives derived from the D-form of the amino acid is more active than that derived from the L-form or the DL-form.

The above compounds are intended only to illustrate the variety of structures, and the above listing is not to be construed as limiting the scope of this invention.

PREPARATION

The preparation of the compounds of this invention involves coupling of an amino acid and a 6-(2-amino-2-arylacetamido)penicillanic acid by the reaction of the carboxy function of the amino acid with the amino function of the 6-(2-amino-2-arylacetamido)penicillanic acid to produce an amide linkage. The compounds of this invention can be prepared by the reaction of the amino acid with the appropriate 6-(2-amino-2-arylacetamido)penicillanic acid in the presence of a condensing agent, e.g., a carbodiimide such as 1,3-dicyclohexylcarbodiimide. Excess carbodiimide is converted to the corresponding urea by acidification, the pH is adjusted to near neutrality and the urea is removed by filtration. The products may be recovered by acidification or extraction.

Additionally, in order to realize the coupling, it is essential, first, that all reactive functionality not participating directly in the reaction be inactivated by appropriate blocking groups, and, secondly, that the carboxy or amino function which is to be coupled by appropriately activated to permit coupling to proceed.

These particular blocking groups which are employed as N-blocking groups are as described herein above.

In rendering the carboxy function active to the coupling reaction, the carboxy function is converted to an acid halide, acid azide, activated ester (e.g., p-nitrophenyl ester) or mixed carbonic anhydride. These acylating agents need not be isolated. It is frequently more convenient and practical to use them in the form of the solution, in which they are prepared.

The conversion of the amino acid or its N-substituted derivative to a mixed carbonic anhydride is effected by dissolving the amino acid or its N-substituted derivative in a ketone solvent containing a tri-(lower)alkylamine and treating the solution with an anhydride forming reagent, e.g., a lower alkyl chloroformate or an aryl chloroformate at a temperature of from 0° to −20° C. The compounds of this invention are obtained by reacting the mixed anhydride with the 6-(2-amino-2-arylacetamido)penicillanic acid at a temperature of about −50° to +50° C. Recovery of the product is effected by precipitation (after acidification of the reaction mixture) or by extraction into an organic solvent such as ethyl acetate, methyl isobutyl ketone or the like, from an acidified reaction mixture.

Further, the 6-(2-amino-2-arylacetamido)penicillanic acid can first be converted to a mono- or disilyl derivative by the reaction with a trialkylsilyl halide or trialkylsilylamine, which is then acylated with an appropriate acylating agent (a carboxylic acid, acid anhydride or acid halide) and hydrolyzed to remove the protecting group.

The N-blocking groups are cleaved in the presence of an acid such as trifluoroacetic acid, p-toluenesulfonic acid or the like, to form the respective acid addition salt products. The cleavage can also be accomplished by hydrogenation in the presence of a catalyst such as palladium, Raney nickel, platinum or rhodium. In general, the hydrogenation is effected in a suitable solvent such as water, methanol, tetrahydrofuran, acetone, acetic acid or the like, at a temperature in the range of 0° to 60° C., and preferably at room temperature. The hydrogen pressure is not critical, and can be below or above atmospheric pressure.

The particular methods of coupling, blocking and cleavage employed in preparing the compounds of this invention are each now well recognized in the art. The conditions under which a particular coupling, blocking or cleavage reaction would be carried out will be apparent to those skilled in the art.

The amino acid derivatives of the 6-(2-amino-2-arylacetamido)penicillanic acids of this invention are of value as additives to materials such as fuels and cutting oils which are subject to bacterial deterioration.

They may be used as antibacterial agents, e.g., in cleaning or disinfecting compositions. They are also remarkably effective in treating a number of infections caused by Gram-negative bacteria including *Esherichia coli, Proteus vulgaris, Proteus mirabillis, Proteus morganii, Klebsiella pneumoniae, Salmonella typhimurium* and *Psudomonas aeruginosa,* and Gram-positive bacteria including *Staphylococcus aureus,* in poultry and animals, including man.

Moreover, some of the compounds of this invention are useful as intermediates in the preparation of the new penicillin derivatives of this invention.

As described above, the compounds of this invention exhibit antibacterial activity against many microorganisms. Their useful activity can be demonstrated by in vitro tests against various organisms.

The compounds of this invention were tested for antibacterial activity according to the following procedure.

Nutrient broth and nutrient agar were prepared according to the conventional procedure. Nutrient agar was used as a vehicle. The stock solution was prepared at 100 μg/ml of the test material in the vehicle. Two-fold dilutions were made with the vehicle and then the diluted stock solution was added to a petri dish and solidified by chilling. Test organisms were grown in the nutrient broth for 20 hours at 37° C. The hardened surface was inoculated with a loopful of the test organism solution containing $1 \times 10^6$ cells per milliliter and incubated for 20 hours at 37° C. At the end of this period, growth of the organism was observed.

The minimum inhibitory concentration (MIC) at which growth of the organism failed to occur was observed and recorded. The following Table 1 summarizes the activity of representative compounds as active antibacterial agents, and compares them with the prior art compounds and the reference drug Sulbenicillin.

In this table, the compounds are shown by indicating R, $R_1$, addition moiety and Y wherein Y is hydrogen or potassium. In addition, the following abbreviations are employed in the specification:

| CBz | Benzyloxycarbonyl |
|---|---|
| Ts | Tosyl |
| Ph | Phenyl |
| iso-Bu | Isobutyl |

TABLE 1

| Compound | | | | | Minimum Inhibitory Concentration (MIC: μg/ml) | | | | | | | | | | | |
|---|---|---|---|---|---|---|---|---|---|---|---|---|---|---|---|---|
| No. | R | $R_1$ | Y | Addition Moiety | Staph. aureus (FDA 209P) | E. coli (NIHJ) | Proteus vulgaris (IFO 3045) | Proteus mirabilis (IFO 3849) | Proteus morganii (IFO 3848) | Klebsiella pneumoniae (ATCC 25955) | Salmonella typhimurium (TA 100)*4 | Psudomonas aeruginosa M-11*1 | Psudomonas aeruginosa M-12*1 | Psudomonas aeruginosa M-16*3 | Psudomonas aeruginosa (ATCC 15691) | Psudomonas aeruginosa (ATCC 15692) |
| 1 | pyrrolidine-NH | (D) H | H | 3H₂O | 0.45 | 6.2 | 1.5 | 1.5 | 3.1 | 50 | | | 3.1 | 3.1 | 12.5 | |
| 2 | pyrrolidine-NCBz | (D) H | K | H₂O | 1.25 | | | | | | | | | | | |
| 3 | pyrrolidine-NH | (D) OH | H | H₂O | 0.9 | 6.2 | 6.2 | 2.2 | 3.1 | | | | | | | 6.2 |
| 4 | pyrrolidine-NH | (L) OH | H | 4H₂O | 1.25 | 25 | 12.5 | 9 | 9 | | | | | | | 50 |
| 5 | pyrrolidine-NCBz | (D) OH | K | | 2.5 | | | | | | | | | | | |
| 6 | pyrrolidine-NCBz | (L) OH | K | | 1.25 | | | | | | | | | | | |
| 7 | piperidine-NH | (D) OH | H | | 1.25 | 25 | <6.2 | 9 | <6.2 | | | | | | | 9 |

TABLE 1-continued

Compound:

$$R-C(=O)-NH-CH(Ar)-C(=O)-NH-CH-CH\underset{S}{\underset{|}{\diagdown}}\underset{|}{\overset{CH_3}{\underset{CH_3}{\diagup}}}C\diagdown CH-CO_2Y$$

where Ar = para-substituted phenyl bearing $R_1$, within a β-lactam ring system.

| No. | R | $R_1$ | Y | Addition Moiety | Staph. aureus (FDA 209P) | E. coli (NIHJ) | Proteus vulgaris (IFO 3045) | Proteus mirabilis (IFO 3849) | Proteus morganii (IFO 3848) | Klebsiella pneumoniae (ATCC 25955) | Salmonella typhimurium (TA 100)*4 | Pseudomonas aeruginosa M-11*1 | Pseudomonas aeruginosa M-12*1 | Pseudomonas aeruginosa M-16*3 | Pseudomonas aeruginosa (ATCC 15691) | Pseudomonas aeruginosa (ATCC 15692) |
|---|---|---|---|---|---|---|---|---|---|---|---|---|---|---|---|---|
| 8 | ⟨piperidine-N-CBz⟩ | (D) | OH | K | | 1.25 | | | | | | | | | | | |
| 9 | ⟨piperidine-N-CBz⟩ | (D) | H | K | | 0.62 | | | | | | | | | | | |
| 10 | ⟨piperidine-N-C(=O)NH_2⟩ | (D) | H | K | | 0.31 | | | | | | | | | | | |
| 11 | ⟨piperidine-N-C(=O)NH_2⟩ | (DL) | H | K | | 0.31 | | | | | | | | | | | |
| 12 | ⟨piperidine-N-H⟩ | (D) | H | H | 4H_2O | 1.25 | | | | | | | | | | | |
| 13 | ⟨piperidine-N-H⟩ | (DL) | H | H | 4H_2O | 3.75 | | | | | | | | | | | |

TABLE 1-continued

| | Compound | | | | | Minimum Inhibitory Concentration (MIC: μg/ml) | | | | | | | | | | |
|---|---|---|---|---|---|---|---|---|---|---|---|---|---|---|---|---|
| No. | R | R₁ | Y | Addition Moiety | Staph. aureus (FDA 209P) | E. coli (NIHJ) | Proteus vulgaris (IFO 3045) | Proteus mirabillis (IFO 3849) | Proteus morganii (IFO 3848) | Klebsiella pneumoniae (ATCC 25955) | Salmonella typhimurium (TA 100)*⁴ | Psudomonas aeruginosa M-11*¹ | Psudomonas aeruginosa M-12*¹ | Psudomonas aeruginosa M-16*³ | Psudomonas aeruginosa (ATCC 15691) | Psudomonas aeruginosa (ATCC 15692) |
| 14 | (indoline NH structure) | (DL) H | H | 2H₂O | 0.31 | | | | | | | | | | | |
| 15 | (tetrahydroisoquinoline NH structure) | (D) H | H | 3H₂O | 0.30 | 25 | 5 | 25 | 25 | 25 | | 25 | 25 | 25 | 50 | |
| 16 | (tetrahydroisoquinoline NH structure) | (DL) H | K | H₂O | 0.46 | | | | | | | | | | | |
| 17 | Ts—N—CH(CH₃)—CH(CH₃) | H | K | H₂O | 0.15 | 25 | 12.5 | 12.5 | 9 | 25 | 12.5 | | | 25 | | |
| 18 | Ts—N—CH(CH₃)—CH(CH₃) | OH | K | H₂O | 0.31 | | | | | | | | | | | |
| 19 | Ts—N—CH(CH₃)—CH(CH₃) | (DL) H | K | H₂O | 0.15 | 25 | 12.5 | 12.5 | 12.5 | | 9 | | | 37 | | |
| 20 | CH₃—N—CH(CH₃)—CH(H)—CH₃ | (D) H | H | 2H₂O | 1.87 | 25 | 6.2 | 9.3 | 9.3 | | | | | 37.5 | | |
| 21 | CH₃—N—CH(CH₃)—CH(H)—CH₃ | (D) OH | H | 2H₂O | 1.87 | 12.5 | 4.7 | 6.2 | 3.1 | | | | | | | |
| 22 | Ts—N—CH₂—CH₃ | H | K | H₂O | 0.31 | 25 | 25 | 25 | 12.5 | | | | | 25 | | |
| 23 | Ts—N—CH(CH₃)—iso-Bu | (D) H | K | | 0.62 | | | | | | | | | | | |

TABLE 1-continued

Compound:

R—C(=O)—NH—CH(—C₆H₄(R₁))—C(=O)—NH—CH—CH—S—C(CH₃)(CH₃)—CH—CO₂Y (penicillin core with N—C=O)

| No. | R | R₁ | Y | Addition Moiety | Staph. aureus (FDA 209P) | E. coli (NIHJ) | Proteus vulgaris (IFO 3045) | Proteus mirabilis (IFO 3849) | Proteus morganii (IFO 3848) | Klebsiella pneumoniae (ATCC 25955) | Salmonella typhimurium (TA 100)[*4] | Psudomonas aeruginosa M-11[*1] | Psudomonas aeruginosa M-12[*1] | Psudomonas aeruginosa M-16[*3] | Psudomonas aeruginosa (ATCC 15691) | Psudomonas aeruginosa (ATCC 15692) |
|---|---|---|---|---|---|---|---|---|---|---|---|---|---|---|---|---|
| 24 | CBz—N(CH₃)—CH(iso-Bu)— | (D) H | K | 5H₂O | 0.62 | 50 | 100 | 100 | 100 | | <6.25 | | | 100 | | |
| 25 | CBz—N(CH₃)—CH(Ph)— | (D) H | K | | 0.62 | 50 | 25 | 25 | 25 | | 12.5 | | | | | |
| 26 | Ts—N(CH₃)—CH(Ph)— | (D) H | K | 2H₂O | 0.62 | | | | | | | | | | | |
| 27 | CH₃—N(H)—CH(iso-Bu)— | (D) H | K | 2H₂O | 3.75 | 50 | 6.2 | 6.2 | 12.5 | | | | | 25 | | |
| 28 | NH (ring) | (D) H | H | 2H₂O | 5.0 | 18.7 | 3.1 | 3.1 | 3.1 | | | | | 37.5 | | |
| 29 | NH (ring) | (D) OH | H | 2H₂O | | | | | | | | | | | | |
| 30 | Sulbenicillin | | | | 1.25 | 12.5 | <3.1 | <3.1 | <3.1 | >100 | | 25 | 25 | 25 | 50 | |

[*1]streptomycin resistant strain derived from Psudomonas aeruginosa (ATCC 15692)
[*2]chloramphenicol resistant strain derived from Psudomonas aeruginosa (ATCC 15692)
[*3]streptomycin, chloramphenicol and mercury resistant strain derived from Psudomonas aeruginosa (ATCC 15692)
[*4]ampicillin resistant strain In general, the compounds of this invention may be utilized in a manner similar to ampicillin and other penicillins. For example, they may be used in various animal species in an amount of about 0.1 to 100 mg/kg daily, orally or parenterally in two to five divided doses to treat infections of bacterial origin.

Having generally described the invention, a more complete understanding can be obtained by reference to certain specific examples, which are included for purposes of illustration only and are not intended to be limiting unless otherwise specified.

EXAMPLE 1

N-benzyloxycarbonyl-D-proline was prepared by the resolution of N-benzyloxycarbonyl-DL-proline as described in the literature (Helv. Chim. Acta, 49 1348 (1966)).

To a solution of 548 mg (2.2 m moles) of N-benzyloxycarbonyl-D-proline and 0.31 ml (2.2 m moles) of triethylamine in 10 ml of acetone, which was cooled to −10° C., there was added dropwise 0.29 ml (2.2 m moles) of isobutyl chloroformate. The mixture was stirred for 15 minutes at −10° C. and then cooled to −40° C. To this mixture was added a solution of 698 mg (2 m moles) of ampicillin, 0.28 ml (2 m moles) of triethylamine and 1 ml of water. The reaction mixture was gradually warmed to 0° C. and stirred for one hour at 0° C. To this reaction mixture, there was added a solution of 218 mg (2.6 m moles) of NaHCO$_3$ in 15 ml of water, and this was stirred for one hour at 0° C. The reaction solution was washed twice with 15 ml of ether, adjusted to pH 2.0 with 6N H$_2$SO$_4$ and extracted successively with 45 ml of methyl isobutyl ketone (hereinafter referred to as MIBK) and 15 ml of MIBK. The MIBK layer was dried over MgSO$_4$ and adjusted to pH 7.0 with potassium 2-ethylhexanoate to precipitate an oily substance. The supernatant was removed by decantation, and the residue crystallized by addition of ether, filtered and dried to give 856 mg (67%) of potassium 6-[D-2-(N-benzyloxycarbonyl-D-prolyl)amino-2-phenylacetamido]penicillanate monohydrate, M.P. 168°–175° C.

Analysis—Calcd. for C$_{29}$H$_{31}$O$_7$N$_4$SK (percent): C, 54.70; H, 5.22; N, 8.80; S, 5.04 Found (percent): C, 54.49; H, 5.90; N, 7.75; S, 4.70; IR (KBr): 3,380, 1,760, 1,650, 1,600 and 1,530 cm$^{-1}$.

The following compounds are prepared in a similar manner:
6-[D-2-(1-benzyloxycarbonyl-4-hydroxyprolyl)amino-2-(4-hydroxyphenyl)acetamido]penicillanic acid
6-[D-2-(1,2,3,4-tetrahydro-2-benzyloxycarbonylisoquinoline-3-carboxamido)-2-(4-hydroxyphenyl)acetamido]penicillanic acid
6-[D-2-(2-benzyloxycarbonylisoindoline-1-carboxamido)-2-(4-hydroxyphenyl)acetamido]penicillanic acid
6-[D-2-(N-tosylprolyl)amino-2-(4-hydroxyphenyl)acetamido]penicillanic acid
6-[D-2-{N-(4-nitrobenzyloxycarbonyl)prolyl}amino-2-phenylacetamido]-penicillanic acid
6-[D-2-(N-tert-butoxycarbonylprolyl)amino-2-phenylacetamido]penicillanic acid
6-[D-2-(N-benzenesulfonyl-N-methylalanyl)amino-2-phenylacetamido]penicillanic acid
6-[D-2-(N-benzenesulfonyl-N-methylalanyl)amino-2-(4-hydroxyphenyl)acetamido]penicillanic acid
6-[D-2-(N-tosylsarcosyl)amino-2-(4-hydroxyphenyl)acetamido]penicillanic acid
6-[D-2-(N-benzyloxycarbonyl-N-methylleucyl)amino-2-(4-hydroxyphenyl)acetamido]penicillanic acid
6-[D-2-(N-tosyl-N-methylalanyl)amino-2-(3-aminophenyl)acetamido]penicillanic acid
6-[D-2-(N-benzyloxycarbonyl-N-methylalanyl)amino-2-(3-aminophenyl)acetamido]penicillanic acid
6-[D-2-(N-tosyl-N-methylleucyl)amino-2-(3-aminophenyl)acetamido]penicillanic acid
6-[D-2-{2-(N-benzyloxycarbonyl-N-methyl)amino-2-phenylacetamido}-2-(4-hydroxyphenyl)acetamido]penicillanic acid
6-[D-2-{2-(N-tosyl-N-methyl)amino-2-phenylacetamido}-2-(4-hydroxyphenyl)acetamido]penicillanic acid

EXAMPLE 2

Into a suspension of 1.00 g of 30% palladium/barium carbonate in 5 ml of water was passed hydrogen for one hour. To this suspension was added a solution of potassium 6-[D-2-(1-benzyloxycarbonyl-D-prolylamino)-2-(4-hydroxyphenyl)acetamido]penicillanate in 10 ml of water. Hydrogen gas was passed into the stirred reaction mixture for one hour and then the catalyst was removed by filtration. The filtrate was adjusted to pH 2.0 with 1N hydrochloric acid, washed three times with 30 ml of ether, adjusted to pH 5.0 with 3% NaHCO$_3$ solution and then concentrated to about 2 ml at a temperature lower than 40° C. to precipitate a crystalline solid which was filtered, washed successively with a small amount of water and acetone, and dried to afford 195 mg (37%) of 6-[D-2-(D-prolylamino)-2-(4-hydroxyphenyl)acetamido]penicillanic acid monohydrate, M.P. 230°–5° C.

Analysis—Calcd. for C$_{21}$H$_{26}$O$_6$N$_4$S$_1$.H$_2$O (percent): C, 52.49; H, 5.87; N, 11.66 Found (percent): C, 52.21; H, 6.27; N, 11.23 IR (KBr): 3,280, 1,760, 1,640, 1,600 and 1,500 cm$^{-1}$.

NMR (100 MHz, DMSO-d$_6$): δ1.50 (s, 6H), 3.98 (s, 1H), 4.0–4.2 (m, 1H), 6.5–6.8 (m, 2H) and 7.0–7.4 (m, 2H) ppm The following compounds are prepared in a similar manner:
6-[D-2-prolylamino-2-(3-aminophenyl)acetamido]penicillanic acid
6-[D-2-prolylamino-2-(4-aminophenyl)acetamido]penicillanic acid
6-[D-2-prolylamino-2-(3-amino-4-hydroxyphenyl)acetamido]penicillanic acid
6-[D-2-(4-hydroxyprolyl)amino-2-(4-hydroxyphenyl)acetamido]penicillanic acid
6-[D-2-(1,2,3,4-tetrahydroisoquinoline-3-carboxamido)-2-(4-hydroxyphenyl)acetamido]penicillanic acid
6-[D-2-(1,2,3,4-tetrahydroisoquinoline-3-carboxamido)-2-(3-aminophenyl)acetamido]penicillanic acid
6-[D-2-(isoindoline-1-carboxamido)-2-(4-hydroxyphenyl)acetamido]penicillanic acid
6-[D-2-(piperidine-2-carboxamido)-2-(3-aminophenyl)acetamido]penicillanic acid
6-[D-2-(N-tosyl-N-methylalanyl)amino-2-(3-aminophenyl)acetamido]penicillanic acid
6-[D-2-(N-methylalanyl)amino-2-(3-aminophenyl)acetamido]penicillanic acid
6-[D-2-(N-methylleucyl)amino-2-(4-hydroxyphenyl)acetamido]penicillanic acid
6-[D-2-(N-methylleucyl)amino-2-(3-aminophenyl)acetamido]penicillanic acid
6-[D-2-(2-methylamino-2-phenylacetamido)-2-(4-hydroxyphenyl)acetamido]penicillanic acid Various other amino acid derivatives of 6-(2-amino-2-arylacetamido)penicillanic acids were synthesized in accordance with the procedure of the above examples, and the results are summarized in the following Table 2, in which the compounds are shown by indicating R, R$_1$, addition moiety and Y wherein Y is hydrogen or potassium, and in which "DMSO" stands for "DMSO-d$_6$"

TABLE 2

Compound:

$$R-\overset{O}{\overset{\|}{C}}-NH-CH-\overset{O}{\overset{\|}{C}}-NH-CH-CH\overset{S}{\underset{N}{\diagdown}}\overset{CH_3}{\underset{C}{\diagup}}\overset{CH_3}{\underset{CH-CO_2Y}{}}$$

with phenyl ring bearing $R_1$ at para position

| No. | R | $R_1$ | Y | Addition moiety | Preparation process (Ex. No.) | Yield (%) | m.p. (°C.) | Elementary analysis Upper: Calcd. Lower: Found C | H | N | S | Impurity | IR (KBr) (cm$^{-1}$) | NMR (100 MHz) δ (ppm) |
|---|---|---|---|---|---|---|---|---|---|---|---|---|---|---|
| 3 | (D) ⟨N–CBz⟩ | OH | K |  | 1 | 77 | 197–200 | 54.87 4.92 8.83 5.05<br>54.43 5.95 7.98 4.65 |  |  |  |  | 3,400, 1,760, 1,650, 1,590, 1,350 | (D$_2$O) 1.42 (s, 6H), 4.10 (s, 1H), 4.60–4.96 (m, 2H), 6.60–6.90 (m, 2H), 6.90–7.40 (m, 7H) |
| 4 | (L) ⟨N–CBz⟩ | H | K | H$_2$O | 1 | 66 | 163–171 | 54.70 5.22 8.80 5.04<br>54.80 5.69 8.76 5.07 |  |  |  |  | 3,400, 1,760, 1,650, 1,515, 1,420, 1,355 |  |
| 5 | (L) ⟨N–CBz⟩ | OH | K |  | 1 | 83 | 200–203 | 54.87 4.93 8.83 5.05<br>54.44 6.30 8.36 4.88 |  |  |  |  | 3,350, 1,760, 1,660, 1,600, 1,510 | (DMSO) 1.40 (s, 3H), 1.51 (s, 3H), 3.84 (s, 1H), 6.48–7.54 (m, 10H) |
| 6 | (DL) ⟨N–Ts⟩ | H | K |  | 1 | 64 | 170–181 | 52.64 4.89 8.77 10.04<br>52.80 5.65 8.19 9.31 |  |  |  |  | 3,380, 1,760, 1,640, 1,590, 1,155 | (D$_2$O) 1.39 (s, 3H), 1.42 (s, 3H), 4.10 (s, 2H), 5.28–5.60 (m, 3H), 6.9–7.7 (m, 9H) |
| 7 | (D) ⟨N–H⟩ | H | H | 3H$_2$O | 2 | 37 | 229–235 | 50.38 6.44 11.19 6.41<br>49.63 5.87 10.81 6.52 |  |  |  |  | 3,380, 3,280, 1,760, 1,665, 1,550 |  |
| 8 | (L) ⟨N–H⟩ | H | H | 3H$_2$O | 2 | 62 |  | 40.81 5.22 9.06 5.19<br>41.03 5.31 9.24 4.88 |  |  |  | Calcd. values corrected for 19% inorganic salts | 3,400, 1,760, 1,630, 1,530 |  |
| 9 | (L) ⟨N–H⟩ | OH | H | 4H$_2$O | 2 | 79 |  | 40.57 5.51 9.01 5.16<br>40.61 5.29 8.53 4.52 |  |  |  | Calcd. values corrected for 14% inorganic salts | 3,400, 1,760, 1,660, 1,510 | (D$_2$O) 1.40 (s, 3H), 1.44 (s, 3H), 4.12 (s, 1H), 4.28–4.58 (m, 1H), 6.88 (d, 2H), 7.26 (d, 2H) |

TABLE 2-continued

Compound $$\underset{R}{\overset{O}{\parallel}}C-NH-\underset{|}{\overset{}{CH}}-\overset{O}{\overset{\parallel}{C}}-NH-\underset{|}{\overset{}{CH}}-\overset{}{\underset{|}{CH}}-\overset{S}{\underset{}{\diagdown}}\overset{CH_3}{\underset{CH_3}{\diagup}}C\overset{CH_3}{\underset{CH_3}{\diagdown}}$$
$$\text{with aryl } R_1 \text{ and } CH-CO_2Y$$

| No. | R | R₁ | Y | Addition moiety | Preparation process (Ex. No.) | Yield (%) | m.p. (°C.) | Elementary analysis Upper: Calcd. Lower: Found C | H | N | S | Impurity | IR (KBr) (cm⁻¹) | NMR (100 MHz) δ (ppm) |
|---|---|---|---|---|---|---|---|---|---|---|---|---|---|---|
| 10 | (D) [pyrrolidinone] | H | K | H₂O | 2 | 23 | 205–210 | 48.82 4.88 / 49.33 5.96 | | 10.85 / 9.28 | 6.21 / 5.56 | | 3,400, 1,770, 1,660, 1,600 | |
| 11 | (L) HO-[pyrrolidine]-CBz | H | H | | 1 | 51 | 157–163 | 58.37 5.41 / 57.65 5.84 | | 9.39 / 9.14 | 5.37 / 5.42 | | 2,920, 1,770, 1,660, 1,510 | (DMSO) 1.40 (s, 3H), 1.54 (s, 3H), 4.12 (s, 1H), 5.20–5.52 (m, 2H), 7.14–7.40 (m, 10H) |
| 12 | (L) HO-[pyrrolidine]-H | H | H | 4H₂O | 2 | 31 | 255–265 | 42.46 5.76 / 42.57 5.65 | | 9.44 / 8.78 | 5.40 / 5.02 | | 3,400, 1,760, 1,640, 1,400 | (DMSO) 1.40 (s, 3H), 1.50 (s, 3H), 4.20–4.42 (m, 2H), 4.54–4.72 (m, 1H), 7.10–7.50 (m, 5H) |
| 13 | (D) [piperidine]-CBz | H | K | | 1 | 84 | 148–156 | 56.94 5.26 / 58.01 6.08 | | 8.85 / 8.90 | 5.07 / 5.24 | | 3,400, 1,760, 1,650, 1,500, 1,260 | (DMSO) 1.38 ((s, 3H), 1.48 (s, 3H), 3.96 (s, 1H), 4.96 (s, 2H), 7.04–7.52 (m, 10H) |
| 14 | (D) [piperidine]-CBz | OH | K | | 1 | 62 | 200–205 | 55.54 5.13 / 54.52 6.08 | | 8.64 / 7.94 | 4.94 / 5.03 | | 3,350, 1,760, 1,660, 1,510, 1,260 | (DMSO) 1.40 (s, 3H), 1.48 (s, 3H), 3.86 (s,1H), 4.60–4.86 (m, 1H), 4.86–5.14 (m, 2H), |
| 15 | (D) [piperidine]-H | H | H | 4 H₂O | 2 | 34 | 35.22 4.84 / 35.55 4.58 | | | 7.47 / 7.39 | 4.27 / 4.15 | Calcd. values corrected for 29% inorganic salts | 3,380, 1,760, 1,650, 1,590, 1,530 | (D₂O) 1.40 (s, 3H), 1.44 (s, 3H), 4.10 (s, 1H), 7.38 (s, 5H) |

TABLE 2-continued

Compound structure:
R—C(=O)—NH—CH(—C₆H₄—R₁)—C(=O)—NH—CH(—S—C(CH₃)₂—)—CH—N—CH—CO₂Y (β-lactam penicillin-type structure)

| No. | R | R₁ | Y | Addition moiety | Preparation process (Ex. No.) | Yield (%) | m.p. (°C.) | Elementary analysis Upper: Calcd. Lower: Found C | H | N | S | Impurity | IR (KBr) (cm⁻¹) | NMR (100 MHz) δ (ppm) |
|---|---|---|---|---|---|---|---|---|---|---|---|---|---|---|
| 16 | (piperidinyl, N—H) | (D) OH | H | — | 2 | 95 | — | 41.55 / 42.11 | 4.38 / 3.58 | 8.82 / 8.28 | 5.05 / 4.52 | Calcd. values corrected for 25% inorganic salts | 3,350, 1,760, 1,660, 1,600, 1,510 | (D₂O) 1.40 (s, 3H), 1.44 (s, 3H), 4.12 (s, 1H), 6.84 (d, 2H), 7.26 (d, 2H) |
| 17 | (tetrahydrothiopyran-CONH₂) | (D) H | K | — | 1 | 14 | ca. 220 | 51.00 / 50.67 | 5.21 / 5.99 | 12.93 / 11.26 | 5.92 / — | | 3,350, 1,760, 1,720, 1,650, 1,590 | (DMSO) 1.40 (s, 3H), 1.45 (s, 1H), 3.88 (s, 1H), 5.16–5.36 (m, 2H), 7.08–7.52 (m, 5H) |
| 18 | (isoindoline N—CBz) | (D) H | K | H₂O | 1 | 56 | 170–175 | 58.43 / 58.21 | 5.05 / 5.65 | 8.02 / 7.81 | 4.59 / 4.63 | | 3,350, 1,760, 1,650, 1,600, 1,390 | |
| 19 | (isoindoline NH) | (D) H | H | 2H₂O | 2 | 19 | 209–214 (dec.) | 57.34 / 57.98 | 5.92 / 5.27 | 10.29 / 10.34 | 5.89 / 5.67 | | 3,400, 1,760, 1,680, 1,540, 1,390, 1,310 | |
| 20 | (isoindoline N—CBz) | (DL) H | K | 2H₂O | 1 | 44 | 152–167 | 56.39 / 56.90 | 5.02 / 5.36 | 7.97 / 7.20 | 4.56 / 4.50 | | 2,950, 1,760, 1,650, 1,600 | |
| 21 | (isoindoline NH) | (DL) H | H | 2H₂O | 2 | 51 | 197–208 | 56.59 / 56.25 | 5.70 / 6.21 | 10.56 / 10.43 | 6.04 / 6.38 | | 3,050, 1,760, 1,650, 1,320 | |

TABLE 2-continued

Compound

R—C(=O)—NH—CH(—C₆H₄—R₁)—C(=O)—NH—CH—CH(—S—C(CH₃)₂—CH(—CO₂Y))—N—C=O

| No. | R | R₁ | Y | Addition moiety | Preparation process (Ex. No.) | Yield (%) | m.p. (°C.) | Elementary analysis Upper: Calcd. Lower: Found | | | | | Impurity | IR (KBr) (cm⁻¹) | NMR (100 MHz) δ (ppm) |
|---|---|---|---|---|---|---|---|---|---|---|---|---|---|---|---|
| | | | | | | | | C | H | N | S | | | | |
| 22 | Ts—N(—CH(CH₃)—CH₃)— (D) | H | K | H₂O | 1 | 76 | 156–161 | 50.29 50.85 | 5.16 5.92 | 8.69 7.55 | 9.94 9.08 | | 2,960, 1,770, 1,660, 1,600 | (D₂O) 1.10 )d, 3H), 1.39 (s, 3H), 1.42 (s, 3H), 2.12 (s, 3H), 2.68 (s, 3H), 4.10 (s, 1H) |
| 23 | Ts—N(—CH(CH₃)—CH₃)— (DL) | H | K | H₂O | 1 | 51 | 173–178 | 50.29 50.15 | 5.16 5.66 | 8.69 8.37 | 9.95 9.61 | | 2,920, 1,760, 1,650, 1,520 | (D₂O) 1.00–1.20 (m, 3H), 1.34, 1.0M, 1.42, 1.46 (6H), 2.80, 2.10 (1H), 2.62, 2.72 (3H), 4.10 (s, 3H) |
| 24 | Ts—N(—CH(CH₃)—CH₃)— (D) | OH | K | H₂O | 1 | 58 | 199–203 | 49.07 50.03 | 5.03 5.89 | 8.48 7.58 | 9.71 8.78 | | 2,950, 1,760, 1,650, 1,590, 1,510 | (D₂O) 1.16(d, 3H), 1.40 (s, 3H), 1.43 (s, 3H), 2.18 (s, 3H), 2.74 (s,3H), 4.10 (s, 1H), 6.74–7.56 (s, 3H) |
| 25 | Ts—N(—CH₂—CH₃)— | H | K | H₂O | 1 | 54 | 170–177 | 49.50 49.20 | 4.95 5.64 | 8.88 7.88 | 10.17 9.07 | | 2,920, 1,760, 1,650, 1,520 | |
| 26 | Ts—N(—CH(CH₃)—iso-Bu)— (D) | H | K | | 1 | 63 | 152–165 (dec.) | 53.87 54.56 | 5.58 6.40 | 8.38 8.05 | 9.59 9.34 | | 2,920, 1,760, 1,640, 1,530 | (D₂O) 2.00–2.16 (3H), 2.64–2.84 (3H), 4.08 (s, 3H) |
| 27 | Ts—N(—CH(CH₃)—Ph)— (D) | H | K | | 1 | 55 | 175–183 | 55.79 55.61 | 4.83 5.28 | 8.13 7.80 | 9.31 8.76 | | 3,370, 1,765 1,650, 1,595, 1,325, 1,160 | |
| 28 | CH₃NH—CH(CH₃)— (D) | H | H | 2H₂O | 2 | 52 | 207–215 | 44.06 44.30 | 5.18 5.24 | 10.28 9.37 | 5.88 5.38 | Calcd. values corrected for 17% inorganic salts | 2,950, 1,760, 1,650, 1,530 | (D₂O) 1.38 (s, 3H), 1.42 (s, 3H), 2.62 (s, 3H), 4.10 (s, 1H), 7.38 (s, 5H) |

TABLE 2-continued

Compound $$R-C(=O)-NH-CH(-C_6H_4-R_1)-C(=O)-NH-CH-CH-S-C(CH_3)(CH_3)-CH-CO_2Y$$ (β-lactam structure)

| No. | R | R$_1$ | Y | Addition moiety | Preparation process (Ex. No.) | Yield (%) | m.p. (°C.) | Elementary analysis Upper: Calcd. Lower: Found | | | | | Impurity | IR (KBr) (cm$^{-1}$) | NMR (100 MHz) δ (ppm) |
|---|---|---|---|---|---|---|---|---|---|---|---|---|---|---|---|
| | | | | | | | | C | H | N | S | | | |
| 29 | CH$_3$NH—CH(CH$_3$)— (D) | OH | H | 2H$_2$O | 2 | 37 | 205–215 | 38.51 / 38.48 | 4.85 / 5.07 | 8.99 / 8.44 | 5.14 / 4.71 | Calcd. values corrected for 22% inorganic salts | 3,400, 1,760, 1,650, 1,610, 1,510 | (D$_2$O) 1.41 (d, CH$_3$), 1.56 (s, 3H), 1.62 (s, 3H), 2.61 (s, 3H), 4.10 (s, 1H) |
| 30 | CBz—N(CH$_3$)—CH(CH$_3$)— (D) | H | K | | 1 | 75 | 140–145 | 55.43 / 54.74 | 5.15 / 5.87 | 9.23 / 8.47 | 5.29 / 4.78 | | 2,950, 1,760, 1,650, 1,520 | (D$_2$O) 1.42 (s, 3H), 1.40 (s, 3H), 2.86 (s, 3H), 4.14 (s, 3H) |
| 31 | CBz—N(CH$_3$)—CH(CH$_3$)— (D) | OH | K | | 1 | 65 | 190–195 | 52.48 / 52.69 | 5.19 / 5.80 | 8.75 / 8.30 | 5.01 / 4.63 | | 2,960, 1,770, 1,650, 1,520 | (D$_2$O) 1.38 (s, 3H), 1.41 (s, 3H), 4.10 (s, 1H), 6.62–7.30 (m, 9H) |
| 32 | BzC—N(CH$_3$)—CH(iso-Bu)— (D) | H | K | 5H$_2$O | 1 | 48 | 150–158 | 53.20 / 53.85 | 6.77 / 6.69 | 8.01 / 6.79 | 4.58 / 4.44 | | 2,950, 1,760, 1,650, 1,540 | |
| 33 | CH$_3$NH—CH(iso-Bu)— (D) | H | H | 2H$_2$O | 2 | 49 | 210–214 | 53.89 / 54.41 | 7.08 / 6.35 | 10.93 / 11.10 | 6.26 / 6.48 | | 2,950, 1,770, 1,650, 1,530 | |
| 34 | CBz—N(CH$_3$)—CH(Ph)— (D) | H | K | | 1 | 46 | 150–158 | 59.26 / 58.50 | 4.97 / 5.61 | 8.38 / 8.09 | 4.80 / 4.94 | | 3,400, 1,765, 1,665, 1,600, 1,495 | |
| 35 | (NH-cycle)— (D) | H | H | 2H$_2$O | 2 | 81 | | 35.38 / 35.38 | 4.15 / 4.38 | 8.25 / 7.54 | 4.72 / 4.18 | Calcd. values corrected for 31% inorganic salts | 3,375, 1,770, 1,660, 1,600, 1,540 | (D$_2$O) 1.40 (s, 3H), 1.44 (s, 3H), 4.12 (s, 1H), 7.14–7.64 (m, 5H) |
| 36 | (NH-cycle)— (D) | OH | H | 2H$_2$O | 2 | 82 | | 34.71 / 34.85 | 4.07 / 4.33 | 8.09 / 7.34 | 4.63 / 4.09 | Calcd. values corrected for 30% inorganic salts | 3,400, 1,760, 1,650, 1,600, 1,510 | (D$_2$O) 1.38 (s, 3H), 1.42 (s, 3H), 4.12 (s, 1H), 6.84 (d, 2H), 7.24 (d, 2H) |

Having now fully described the invention, it will be apparent to one of ordinary skill in the art that many changes and modifications can be made thereto without departing from the spirit or scope of this invention as set forth herein.

What is claimed as new and intended to be covered by Letters Patent is:

1. 6-(D-2-prolylamino-2-phenylacetamido) penicillanic acid and non-toxic pharmaceutically acceptable salts thereof.

* * * * *

UNITED STATES PATENT AND TRADEMARK OFFICE
CERTIFICATE OF CORRECTION

PATENT NO. : 4,179,437
DATED : December 18, 1979
INVENTOR(S) : YOSHIHARU MORITA ET AL It is certified that error appears in the above–identified patent and that said Letters Patent are hereby corrected as shown below:

Please change the third line of priority data to appear as follows:

[30]   --Feb. 6, 1976   [JP]        Japan.....51/12119

Signed and Sealed this

Fifteenth Day of April 1980

[SEAL]

Attest:

SIDNEY A. DIAMOND

Attesting Officer    Commissioner of Patents and Trademarks